United States Patent [19]

Heyrend et al.

[11] Patent Number: 6,044,292
[45] Date of Patent: Mar. 28, 2000

[54] APPARATUS AND METHOD FOR PREDICTING PROBABILITY OF EXPLOSIVE BEHAVIOR IN PEOPLE

[76] Inventors: F. LaMarr Heyrend, 411 N. Allumbaugh; Donald R. Bars, 5121 N. Mountain View, both of Boise, Id. 83704

[21] Appl. No.: 09/158,190

[22] Filed: Sep. 21, 1998

[51] Int. Cl.$^7$ .......................... A61B 5/0484; A61B 5/0476
[52] U.S. Cl. .......................... 600/544; 600/545; 600/558; 128/898
[58] Field of Search .................................. 600/300, 701, 600/544, 545, 546

[56] References Cited

U.S. PATENT DOCUMENTS

| | | | |
|---|---|---|---|
| 4,862,359 | 8/1989 | Trivedi et al. | 364/413.05 |
| 5,320,109 | 6/1994 | Chamoun et al. | 28/731 |

OTHER PUBLICATIONS

Medical Procedure Patents, the 1996 Amendment and Who is Really Liable, an article by Randall R. Bateman and W. Wayne Western of Thorpe, North & Western, Intellectual Property Today, Dec. 1997.

Handbook of Psychophsiology, edited by Norman S. Greenfield, University of Wisconsin and Richard A. Stenback, University of California at San Diego.

First Reading: QEEG and Evoked Potentials, Treasure Valley Neuroscience Center, 321 N. Allumbaugh, Boise, Idaho 83704.

Pattern Reversal Visual Evoked Potentials and Explosive Behaviors, by F. LaMarr Heyrend, Donald R. Bars, C. Dene Simpson, James C. Munger, Zane Nelson and John Burns (corresponding author: Donald R. Bars, Ph.D.

*Primary Examiner*—Cary O'Connor
*Assistant Examiner*—Michael Astorino
*Attorney, Agent, or Firm*—Frank J. Dykas; Robert L. Shaver

[57] ABSTRACT

A method and apparatus for determining the probability of explosive behavior in a person of known age, sex and use of medication, is provided by generating and measuring a visually evoked response to a certain visually displayed paradigm and measuring the amplitude, in microvolts, of the evoked response at approximately 100 milliseconds after cessation of the paradigm display, and quantifying the absolute values of the delta, theta, alpha and beta frequency bands of a standard EEG, and applying this data to an algorithm to compute on the probability of explosive behavior.

8 Claims, 4 Drawing Sheets

APPARATUS AND METHOD FOR PREDICTING PROBABILITY OF EXPLOSIVE BEHAVIOR IN PEOPLE

BACKGROUND OF THE INVENTION

1. Technical Field

This invention generally relates to an apparatus and method for predicting the propensity of any individual for exhibiting explosive behavior by obtaining and processing electroencephalographic information and applying that data to an algorithm to compute the probability of explosive behavior.

2. Background

With each violent outburst by an adolescent in our society, the pressing need for early identification of children who exhibit explosive, aggressive, uncontrollable outbursts becomes more critical. The high incidence of this behavior disorder during elementary school years and the evidence that such disorders may be precursors of adult sociopathy and psychopathology makes it important that these children be identified and properly treated.

In the past, explosive behavior in children and adolescents was often times treated as a symptom of some other behavior or mood disorder, such as attention deficit/hyperactivity disorder, which is defined in the American Psychiatric Association's Diagnostic and Statistical Manual of Mental Disorders, Fourth Edition, as "a persistent pattern of inattention and/or hyperactivity-impulsivity that is more frequent and severe than is typically observed in individuals at a comparative level of development, which clearly interferes with developmentally appropriate social, academic or occupational functioning". In other cases, it is associated as a symptom of a mood disorder, such as a major depressive disorder or bipolar I or II disorders. Explosive behavior is not generally considered as an independent disorder of its own right.

Yet, at the same time it is known that psychotherapy is not an effective method of treatment for explosive behavior.

A considerable amount of research has been undertaken in the prior art to learn more about the biological basis for what are commonly called genetic-environmental interactions which occur because of environmental effects. It is also generally believed, and the evidence supports, a correlation between a high incidence of explosive behavior during elementary school years and adult sociopathy and psychopathology.

While it is known that explosive behavior frequently has an organic or biological component, its exact etiology can be due to various neurological substrates. Prior art studies of prison inmates have found that over half had abnormal electroencephalograms and that a significant majority of these abnormalities involve the temporal lobes.

It is also known that the use of certain types of medications, including anti-convulsant medications, can result in significant and effective control of explosive behavior symptoms and the use of other types of medications, such as stimulants and antidepressants will aggravate the symptoms of explosive behavior.

Accordingly, what is needed is a means of identifying children and adolescents who have the biological predisposition toward explosive behavior, either before the explosive behavior manifests itself, or at the very least, where some explosive behavior is already manifesting, but to an insufficient degree to rely on the diagnosis of the behavior as being present.

DISCLOSURE OF INVENTION

These objects are achieved using a testing apparatus which includes an EEG Data Acquisition and Analysis System, which is electrically interconnected to a head assembly containing a plurality of EEG electrodes. The output from the EEG Data Acquisition and Analysis System is sent to a microprocessor where two primary functions of the testing system are performed. These are, the quantification of a standard EEG into absolute powers in the delta, theta, alpha and beta frequency bands and the timing, synchronization and averaging of a series of displays of a paradigm generating a visually evoked response.

Also electrically interconnected to the microprocessor is a visual display device for periodically displaying a plurality of sequential, visual paradigms to a test subject. Hard copy output devices, such as a printer and a video output are also interconnected to the microprocessor.

In use, the testing system is used to test for the probability of explosive behavior. The individual to be tested is first seated comfortably in a chair and sixteen (16) electrodes are attached to the scalp of the individual to be tested in accordance with the International 10-20 System of the American Electroencephalographic Society's guidelines, namely to locations F7, F3, F4, F8, T3, C3, CZ, C4, T4, T5, PE, PZ, P4, T6, 01 and 02. Electrode impedance is maintained at less than 2.0 Kohms and the impedance between homologous sites maintained within 1.0 Kohms. The gain for the EEG Data Acquisition and Analysis System is set at 30,000, with a low pass filter at 100 Hz, and a high pass filter at 1.0 Hz, and a 60 Hz notch filter is set in.

A standard quantitative electroencephalogram is then performed, at which time the EEG Data Acquisition and Analysis System, working in conjunction with the microprocessor, provides a measurement as to the absolute power of the electroencephalograph in the delta, theta, alpha and beta frequency bands, all in the absence of any visual or auditory stimulus.

Next, a visually evoked potential test is conducted using a pattern/reversal visual evoked checkerboard paradigm, using 19 mm black and white alternating squares displayed on the visual device at eye level, 76 cm in front of, and subtending a visual angle of 23 degrees of the individual being tested. The pattern is reversed every 0.59 seconds for a total of 1.7 stimuli per second. A 256 millisecond epoch is utilized with a five millisecond pre-stimulus time. The flash paradigm utilizes a 512 millisecond epoch with 10 milliseconds of pre-stimulus time. The intensity of stimulus from the checkerboard pattern/reversal is 12.69 candelas per square meter, and the flash is 19.26 candelas per square meter. The test subject is instructed to visually fixate on a red dot centered on the visual device, is requested not to speak, and to remain relaxed with as little movement as possible throughout the two minutes of recording time.

The visually evoked response to each display of a paradigm, as recorded by the EEG Data Acquisition and Analysis System, is then recorded in the microprocessor in a synchronized manner with the time of the display of the paradigm and then averaged together to cancel out the potentials of brain activities that are not related to the visually evoked response, thus generating, in microvolts, the potential of the visually evoked response over a period of time from immediately prior to the display of the paradigm to the time of approximately 300 milliseconds after cessation of the displayed paradigm.

The test subject is also interviewed, or in some other way, certain biographical and medical data is acquired for use in the analysis conducted in the microprocessor to determine the probability of explosive behavior. The information required is the identification on the sex of the test subject, the test subject's age, and a medical history of the test subject, including whether or not the test subject is currently taking any medications.

Next, one of three algorithms are applied to the data. The first algorithm is applicable to any test subject, irrespective of whether or not the test subject is using medication or other drugs at the time of testing. This algorithm is: ln(P [explosive])=−6.2036+0.1194*age+(−0.7567*sex) +0.1743*meds+1.0754*lnDeltaF4+0.2281*maxP100. In it: age means the test subject's age in years; sex means, in the case of a male test subject, the value of 0, and in the case of a female test subject the value of 1; meds means, in case the individual is taking medication, a value of 1, and in the case where the test subject is not taking medication, a value of 0; and lnDeltaF4 means the natural log of the absolute value, in microvolts of the Delta wave band, as taken at the electrode placement location F4 as shown in FIG. 2; and MaxP100 means the maximum positive voltage potential, in microvolts, of the visually evoked response at a time of approximately 100 milliseconds after termination of the visual display of the paradigms as averaged as previously described. It can be used to determine a probability of explosive behavior irrespective of the age, sex or medical condition of the test subject by taking $e^{ln(P[explosive])}$.

In the case where it is reliably determined that the test subject is not on medication, then a second algorithm can be applied to the data. The second algorithm is: ln(P [explosive])=−8.0905+0.1348*age+(−0.7848*sex)+ 1.4233*lnDeltaF4+(−2.3854*lnAlphaF3)+ 2.4054*lnAlphaF4+0.2521*maxP100. The terms previously defined for the first algorithm remain the same, and in addition, lnAlpha F3 means the natural log of the absolute power of the alpha band width taken at electrode location F3; and, lnAlpha F4 means the natural log of the absolute power of the alpha band width taken at electrode location F4.

In the event that it can be reliably determined that the test subject is on medication at the time of testing, then a third algorithm may be used, as follows: ln(P[explosive])= 3.6891+(−0.0211*age)+6.0591*sex+(−2.214*lnAlphaCZ)+ 2.3227*lnDeltaF4+2.4516*lnAlphaF4+2.1643*lnDelta02+ (−3.0554*lnDeltaT6)+(−1.6841*sex*lnDelta02), with the definitions again being the same as for the first and second algorithms taken at various different electrode placements.

In each case, the probability of explosive behavior can then be determined by taking $e^{ln(P[explosive])}$.

BEST MODE FOR CARRYING OUT INVENTION

What follows is a description of an apparatus and method of testing individuals to determine a probability of future explosive behavior. While this apparatus is used to determine a probability of future explosive behavior with a high degree of concordance between test results and clinical evaluations, the absence of positive test results, that is to say a finding of low probability of explosive behavior, does not mean that the tested individual is not predisposed toward explosive behavior, as there are many factors, biological and environmental, which can create multiple paths and mechanisms which can result in an individual's manifestation of explosive behavior.

Figure 1:
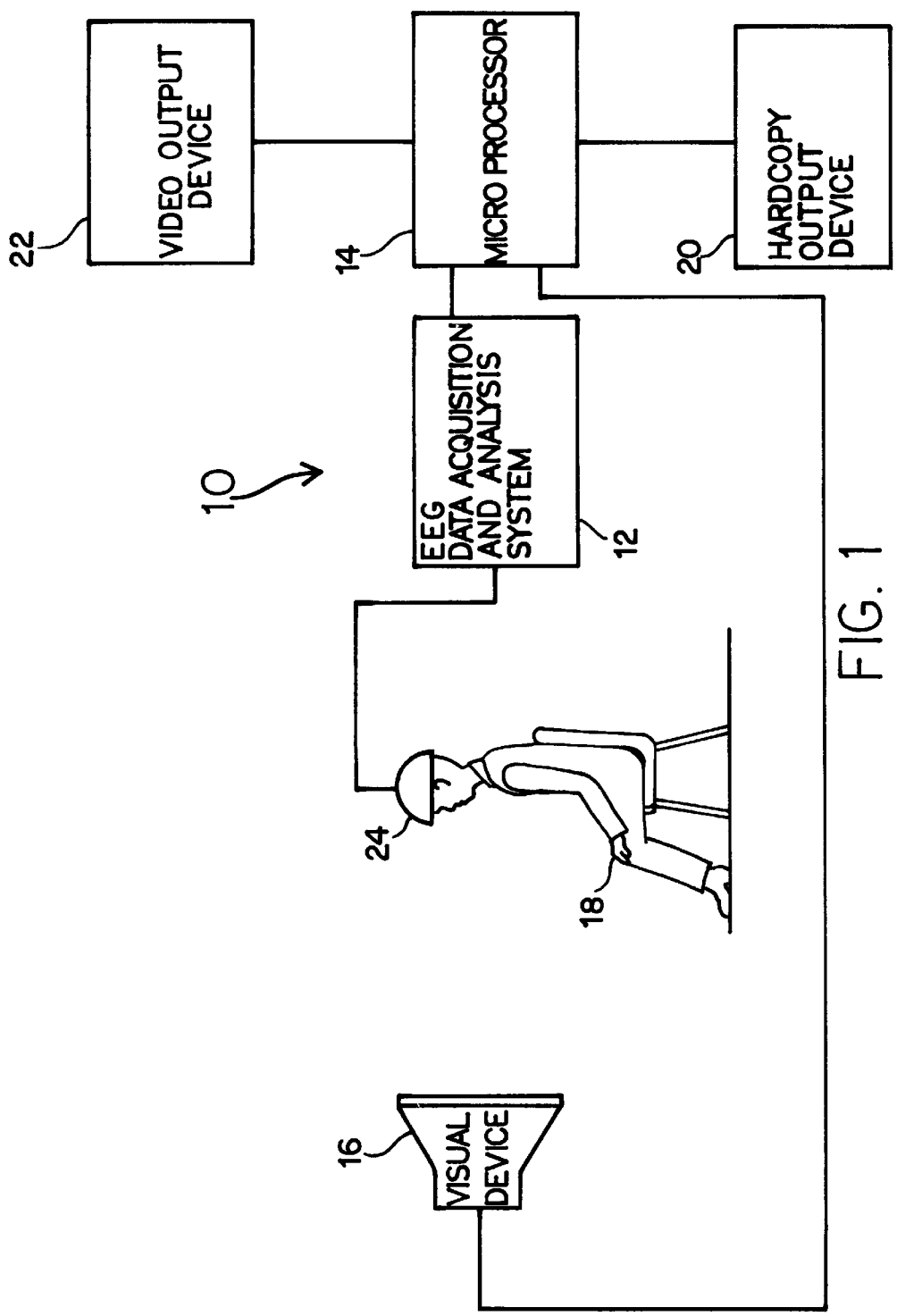
FIG. 1 is a representational schematic of the testing apparatus.

Referring now to FIG. 1, there is shown in representational schematic format the apparatus, or testing system 10. At the heart of testing system 10 is EEG Data Acquisition and Analysis System 12, which is electrically interconnected to a head assembly 24 containing a plurality of EEG electrodes. EEG Data Acquisition and Analysis System 12 output is sent to microprocessor 14 where two primary functions of the testing system 10 are performed.

Also electrically interconnected to microprocessor 14 is visual device 16, which is used to periodically display a plurality of sequential visual paradigms to test subject 18. The two functions performed in microprocessor 14 are the quantification of a standard EEG into absolute powers in delta, theta, alpha and beta frequency bands, and the second function being the timing, synchronization and averaging of the visually evoked responses to a periodic display of a paradigm using visual device 16. Averaging is used to average out random waves and thus quantify the actual visual evoked response over a period of time relative to each of the sequential paradigm displays.

Hard copy output device 20 is also provided, and typically is a standard printer capable of generating tables of data and accurate graphic displays. Video output device 22, typically a standard high resolution video display screen is used for real time displays of the same data.

Figure 2:
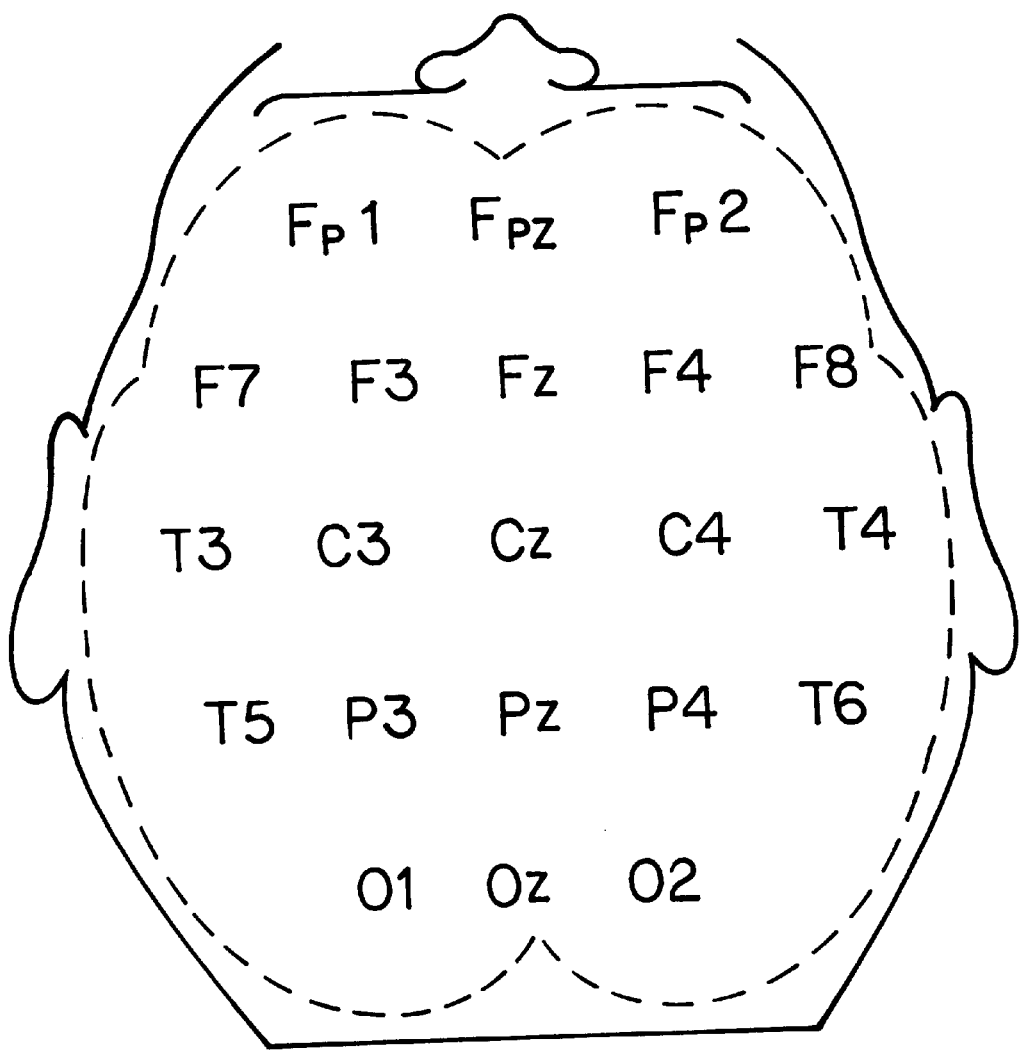
FIG. 2 is a representational map of the scalp of a person showing the location and designator for standard electrodes at standard sites in accordance with the American Electroencephalographic Society's Electrode Placement International 10-20 Standard System for measuring a person's brain waves.

To use system 10 to test for the probability of explosive behavior, the individual to be tested, 18, is first seated comfortably in a chair and sixteen electrodes contained within head assembly 24 are attached to the scalp of the individual to be tested in accordance with the International 10-20 System of the American Electroencephalographic Society's guidelines, namely to locations F7, F3, F4, F8, T3, C3, CZ, C4, T4, T5, PE, PZ, P4, T6, 01 and 02, as shown in FIG. 2. Electrode impedance is maintained at less than 2.0 Kohms and the impedance between homologous sites maintained within 1.0 Kohms. The gain for EEG Data Acquisition and Analysis System 12 is set at 30,000, with a low pass filter at 100 Hz, and the high pass filter at 1.0 Hz, and a 60 Hz notch filter is set in.

A standard quantitative electroencephalogram is then performed, at which time EEG Data Acquisition and Analysis System 12, working in conjunction with microprocessor 14, provides a measurement as to the absolute power of the electroencephalo-graph, in delta, theta, alpha and beta frequency bands, all in the absence of any visual or auditory stimulus. This may all be accomplished in accordance with the teachings of U.S. Pat. No. 4,862,359, dated Aug. 29, 1989, the teachings of which are herein incorporated by reference.

Figure 3:
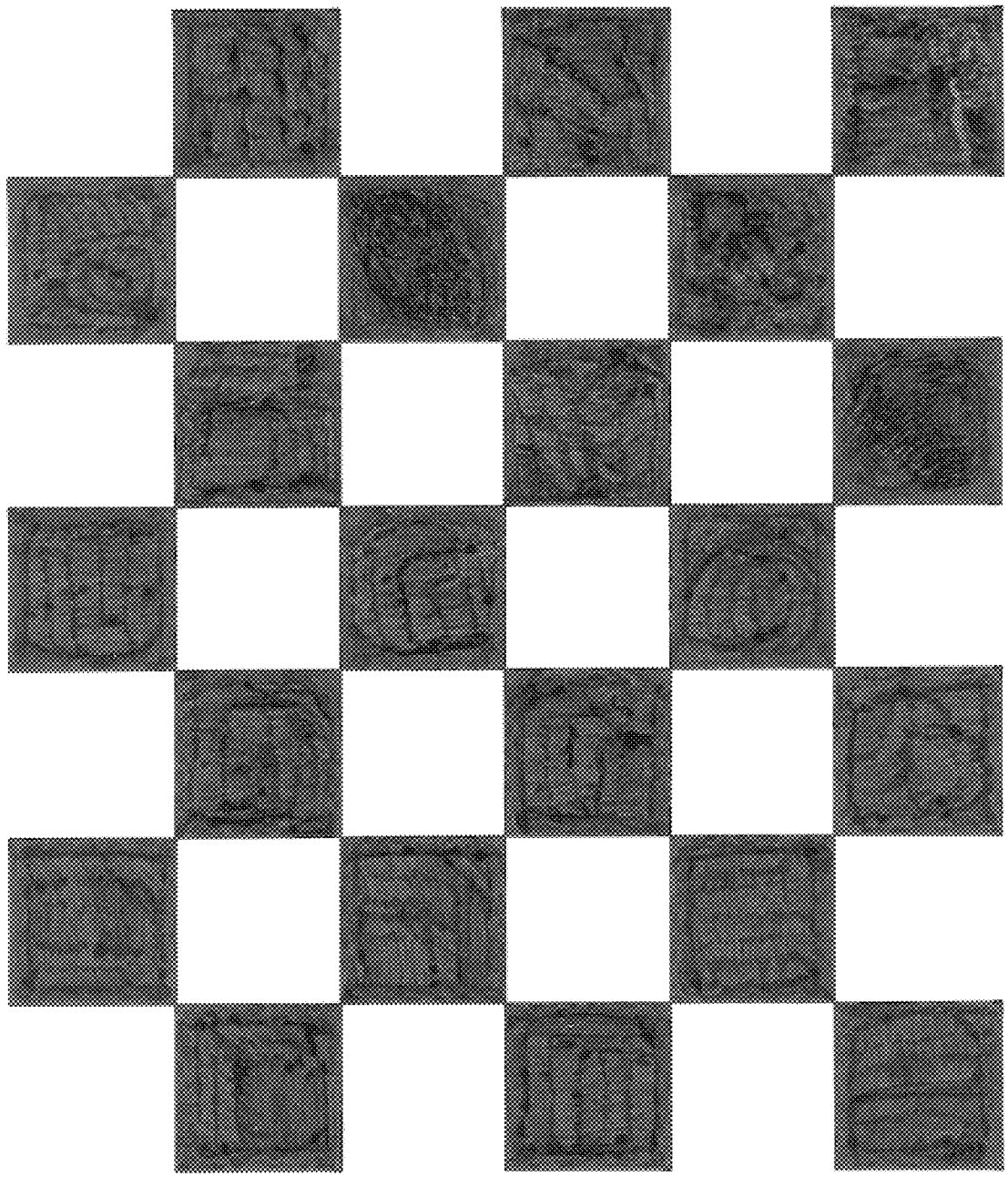
FIG. 3 is a representational drawing of a checkerboard pattern/reversal paradigm used in the present invention to generate visually evoked potentials in the brain.

Next, a visually evoked potential test is conducted using a pattern/reversal visual evoked, checkerboard paradigm, as shown in FIG. 3, using 19 mm black and white alternating squares displayed on visual device 16 at eye level, and 76 cm in front of, and subtending a visual angle of 23 degrees of test subject individual 18. The pattern is reversed every 0.59 seconds for a total of 1.7 stimuli per second. A 256 millisecond (ms) epoch is utilized with a five ms pre-stimulus time. The flash paradigm utilizes a 512 ms epoch with 10 ms of pre-stimulus time. The intensity of stimulus from the checkerboard pattern/reversal is 12.69 candelas per square meter (cd/m$^2$), and the flash is 19.26 cd/m$^2$. The test subject 18 is instructed to visually fixate on a red dot centered on visual device 16, is requested not to speak, and to remain relaxed with as little movement as possible throughout the two minutes of recording time.

The visually evoked response to each display of a paradigm, as recorded by EEG Data Acquisition and Analysis System 12, is then recorded in microprocessor 14 in a synchronized manner with the time of the display of the paradigm, and then averaged together, to cancel out the potentials of brain activities that are not related to the visually evoked response, thus generating, in microvolts, the potential of the visually evoked response over a period of time from immediately prior to the display of the paradigm to the time of approximately 300 milliseconds after cessation of the displayed paradigm.

The test subject 18 is also interviewed, or in some other way, certain biographical and medical data is acquired for use in the analysis conducted in microprocessor 14 to determine the probability of explosive behavior. The information required is the identification on the sex of the test subject, the test subject's age, in years, and a medical history as to whether or not the test subject is currently taking medications such as anti-depressants, anti-convulsants, alpha blockers, stimulants, lithium, tricyclic anti-depressants, or any other type of drug or medication.

Next, in the preferred embodiment of the present invention, one of three algorithms is applied in microprocessor 14 to the data collected to determine a probability for explosive behavior. These Algorithms are as follows:

A first algorithm may be used irrespective of whether test subject 18 is, or is not, using medication or other drugs at the time of testing. The first algorithm is: ln(P[explosive])=−6.2036+0.1194*age+(−0.7567*sex)+0.1743*meds+1.0754*lnDeltaF4+0.2281*maxP100, and can be used to determine a probability of explosive behavior irrespective of the age, sex or medical condition of the test subject. In it: ln(P[explosive]) means the natural log of the probability of explosive behavior. Actual probability of explosive behavior can then be determined by taking $e^{ln(P[explosive])}$; age means the test subject's age in years; sex means, in the case of a male test subject, the value of 0, and in the case of a female test subject the value of 1; meds means, in case the individual is taking medication, a value of 1, and in the case where the test subject is not taking medication, a value of 0; and lnDeltaF4 means the natural log of the absolute value, in microvolts, of the Delta wave band, as taken at the electrode placement location F4 as shown in FIG. 2; and MaxP100 means the maximum positive voltage potential, in microvolts, of the visually evoked response at a time of approximately 100 milliseconds after termination of the visual display of the paradigms as averaged as previously described.

In the case where it is reliably determined that the test subject is not on medication at the time of testing, then, in the preferred embodiment, the following algorithm may be applied to the data obtained from testing system 10 to determine the probability of explosive behavior, as follows:

ln(P[explosive])=−8.0905+0.1348*age+(−0.7848*sex)+1.4233*lnDeltaF4+(−2.3854*lnAlphaF3)+2.4054*lnAlphaF4+0.2521*maxP100. The terms previously defined for the first algorithm remain the same, and in addition, lnAlpha F3 means the natural log of the absolute power of the alpha band width taken at electrode location F3; and, lnAlpha F4 means the natural log of the absolute power of the alpha band width taken at electrode location F4.

In the event it can be reliably determined that the test subject is on medication at the time of testing, then a third algorithm may be used, as follows: ln(P[explosive])=−3.6891+(−0.0211*age)+6.0591*sex+(−2.214*lnAlphaCZ)+2.3227*lnDeltaF4+2.4516*lnAlphaF4+2.1643*lnDeltaO2+(3.0554*lnDeltaT6)+(−1.6841*sex*lnDeltaO2), with the definitions again being the same as for the first and second algorithms taken at various different electrode placements as set forth in FIG. 2.

Figure 4:
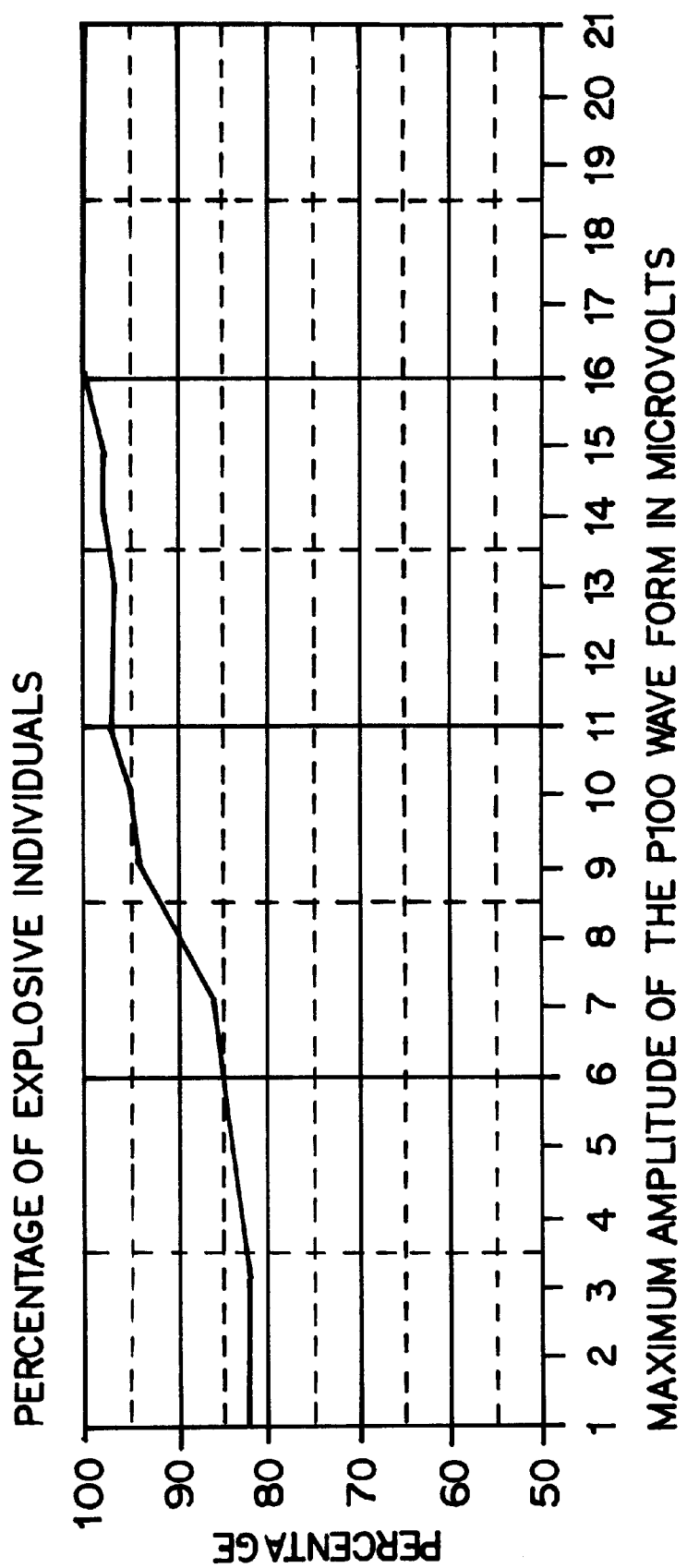
FIG. 4 is a graph showing the percentage of explosive individuals in relationship to the amplitude of the visually evoked potential 100 milliseconds after termination of the display of the paradigm of FIG. 2.

In practice it has been found that the determination of the maximum potential of the visually evoked response, in microvolts, at approximately 100 milliseconds after termination of the stimulus of the visual display of the paradigm is a most significant indicator of the probability of explosive behavior for those tested individuals who are determined not to be taking medication at the time of testing, and, if the first algorithm is used, for any individual irrespective of whether medication is being used or not. In fact, it appears, as can be seen in the graph of FIG. 4, as the amplitude of the visually evoked response at approximately 100 milliseconds after termination of the stimulus increases, the percentage of probability of explosive behavior correspondingly increases, and at amplitudes greater than 16 microvolts, there appears to be a 100% probability of future explosive behavior in the tested individual.

These results and the algorithms used were tested on a test group of children and adolescents selected from a group of 454 children. Complete medical data and clinical evaluations were available for 326 of the children, which became the test group. One hundred ninety seven were not on medication at the time they were subjected to testing through system 10. In the study were 105 females and 221 males, of which 80 females and 187 males with an average age of 13.03 years were explosive, with the remainder not testing positive for explosive behavior and of an average of 14.32 years.

Each patient was administered a series of evoked potential studies and a quantitative electroencephalogram, in accordance with the American Electroencephalographic Society's Guidelines, utilizing the Brain Atlas III Ô® of the Bio-Logic Systems Corporation, Chicago, Ill. Electrode placements were in accordance with the International 10-20 system, using an Electro-CapÔ®, with 16 active electrodes; F7, F3, F4, F8, T3, C3, CZ, C4, T4, T5, P3, Pz, P4, T6, 01, and 02. A monopolar montage with forehead ground was utilized with linked ear reference. Electrode impedance was maintained less than 2.0 Kohms and the impedance between homologous sites maintained within 1.0 Kohms. The gain was set at 30,000, the low pass filter at 100 Hz, the high pass filter at 1.0 Hz, and the 60 Hz notch filter was set in. Patients were comfortably seated in a padded reclining chair in a small, sound attenuated room. A channel-by-channel calibration was performed before and after each recording session.

The electrophysiological test series consisted of: (1) four visual evoked potentials (VEP), pattern reversal (both eyes, left eye, right eye), and flash (both eyes); (2) three auditory evoked potentials (AEP) which is commonly known as the odd ball paradigm at 3 different speeds; (3) two brainstem auditory evoked potentials (BAER); and (4) twenty minutes (post 2 minutes hyperventilation) of computerized electroencephalogram (CEEG). The digital EEG data was evaluated and artifact free data was used to create eyes open and eyes closed (resting) Fast Fourier Transformed files (FFT). All of the VEP's, some AEP and the FFT files were analyzed in the study.

The pattern/reversal visual evoked potential was recorded from each individual in accordance with the American Electroencephalographic Society's Guidelines. The checkerboard pattern/reversal paradigm utilized 19 millimeter, black and white alternating squares displayed on a model TC1115 RCA monitor positioned at eye level, 76 centimeters in front of the patient and subtending at a visual angle of 23 degrees. The pattern reversed every 0.59 seconds for a total of 1.7 stimuli per second. A 256 millisecond (ms) epoch was utilized with a five ms pre-stimulus time. The flash paradigm utilized a 512 ms epoch with 10 ms of pre-stimulus time. The intensity of stimulus from the checkerboard pattern/reversal was 12.69 candelas per square meter ($cd/m^2$) and the flash 19.26 $cd/m^2$. The patient was instructed to visually fixate on a red dot, centered on the RCA monitor, requested not to speak, and, to remain relaxed with as little movement as possible throughout the two minutes of recording time. Artifacts were detected and removed using the Bio-Logic on-line artifact reject program. For each patient, two hundred artifact-free trials were averaged together to produce the final waveform.

All patient clinical files were reviewed for presence of: head injuries, loss of consciousness, or explosive behaviors, defined as any mention of: explosive rage, out-of-control anger, out-of-control aggression, verbal or physical attacks on another individual, Intermittent Explosive Disorder, or Episodic Dyscontrol Syndrome. These variables were evaluated across the pattern/reversal averaged visually evoked potential amplitude measured in negative microvolts, at approximately 75 ms after termination of the stimulus (N75) and the positive amplitude, measured in microvolts, at approximately 100 ms after termination of the stimulus (P100), recorded over the occipital lobes by 01 and 02 scalp electrodes, the common method of recording this phenomenon.

Logistic regression analysis was then used to determine if the response variable, explosivity, was significantly associated with any of 34 predictor variables measured, namely a history of head injury, loss of consciousness, sex, age, maximum amplitude of the N75 and P100 wave forms and the absolute power of the delta, theta, alpha and beta frequency bandwidth. Explosive behaviors were found in 268 (82%) of the 328 patients in the study, 162, or 81% of the 199 patients were not on medication at the time of their study.

The highest voltage recorded during the VEP, at either 01 or 02 electrodes was analyzed for each patient. Patients qualifying as explosive were significantly more likely to have increased P100 amplitude values ($\chi^2$=24.9026, df=1; p<0.0001) and there were significantly more males ($\chi^2$=7.0423, df=1; p<0.008). The explosive patients averaged 10.31 mV (SD=4.96) and the nonexplosive patients averaged 6.89 mV (SD=2.6). Evaluating the data on the nonmedicated patients again showed a relationship between an increase in amplitude of the P100 and explosive behavior ($\chi^2$=18.1592, df=1; p<0.0001). The variable of sex was only slightly significant ($\chi^2$=4.055, df=1); p<0.044). The explosive patients averaged 10.41 mV (SD=4.78) and the nonexplosive patients averaged 6.8 mV (SD=2.36). No other predictor/response relationships were statistically significant. FIG. 4 depicts the percentage of explosive patients based upon the amplitude of the P100 wave form. It shows that 50% of the explosive patients in our study produce a P100 wave form of 9.0 mV or greater.

Our testing showed that high amplitude P100 wave forms are significantly associated with the behavior exhibited by one subset of aggressive, explosive individuals. We believe that this wave form, which occurs within the obligatory portion of the brain's electrophysiological response to sensory stimulation, approximately within the first 200 milliseconds, post stimulus, is a biological signature and represents an individual's unique biological predisposition to respond to some environmental situations in a given manner, namely explosively. We have also shown that this relationship and its significance does not change when patients on medication are included in the statistical analysis. The study strongly suggests that many individuals exhibiting explosive behaviors have an organic predisposition for violent or explosive behavior which is an innate characteristic of their central nervous system and that the use of non-invasive visual evoked potentials can accurately identify this group of biologically based explosive disorders.

Concordance testing was then conducted, in which all possible paring of individuals with explosive behavior present and explosive behavior absent were created. A pair was defined as concordant if the individual with explosive behavior present was also the individual predicted by the logistical regression models of the aforementioned algorithms to be an individual more likely to have explosive behavior present, based upon physiological predicted variables, primarily the amplitude of the visually evoked potential at approximately 100 milliseconds after stimulus. A pair was discordant if the model incorrectly predicted that the individual with explosive behavior absent was more likely to be the individual with explosive behavior present. The percentages of the total number of pairs that were concordant was 80%, and discordant 19.8%.

It should be apparent to those skilled in the art that if a different paradigm or paradigm display procedure were to be used, a different visually evoked response would be generated. However, while this may generate a different set of significant variables in the algorithms, standard logistical regression analysis procedures could be used, as set forth above, to generate similar algorithms to those set forth in this preferred embodiment, which in and of themselves may be of similar high reliability.

While there is shown and described the present preferred embodiment of the invention, it is to be distinctly understood that this invention is not limited thereto but may be variously embodied to practice within the scope of the following claims.

I claim:

1. A method of determining the probability of explosive behavior in a person of known age, sex and use of medication, using an electroencephalographic machine operable for reading human brain waves and generating an output, a computer operable for receiving the output of said electroencephalographic machine, a device operable to display a paradigm of a pre-selected design, illumination, and frequency, said computer also capable of synchronizing the recording and averaging said brain waves when the paradigm is illuminated, which comprises:

attaching electrodes of an electroencephalographic machine to the scalp of said person in accordance with the American Electroencephalographic Society's Electrode Placement International 10-20 Standard System for measuring a person's brain waves;

positioning said person to view a paradigm to visually evoke a potential in said person's brain;

displaying to said person a plurality of sequentially displayed paradigms and simultaneously measuring the brain waves of said person for each of the displayed paradigms during the time of display;

averaging said brain waves to determine the visually evoked potential to said displays of said paradigms;

measuring the maximum amplitude, in microvolts, of said visually evoked potential at a point in time approximately 100 msec. after termination of each of the displays of said paradigms;

conducting and recording the quantitative electroencephalographic activity of said person;

measuring the amplitude of said quantitative electroencephalographic activity;

conducting a logistic regression analysis of said visually evoked potential at approximately 100 msec. after termination of each of said displays of said paradigm, said electroencephalographic activity, and said person's age, sex, and whether said person is taking medication, to establish a predictive algorithm; and computing the probability of explosive behavior using said algorithm.

2. The method of claim 1 wherein the steps of conducting a logistic regression analysis of said visually evoked potential at 100 msec. after termination of each of said displays of said paradigm, and said person's age, sex, and whether said person is taking any medication, to establish a predictive algorithm, and computing the probability of explosive behavior using said algorithm further comprise:

measuring the absolute power of the Delta frequency band at electrode F4; and computing the probability of explosive behavior using the algorithm ln(P[explosive])=−6.2036+0.1194*age+(0.7567*sex)+0.1743*meds+1.0754*lnDeltaF4+0.2281*maxP100, where (P[explosive]) means the probability of explosive behavior, age means the person's age in years, sex has a value of 0 if said person is a male and a value of 1 if said person is a female, meds has a value of 1 if said person is taking medications and 0 if not taking medications, DeltaF4 means the log of the absolute power of the Delta frequency band taken at electrode F4, and maxP100 means the maximum amplitude, in microvolts of said visually evoked potential at a point in time approximately 100 msec. after termination of the displays of said paradigms.

3. An apparatus for determining the probability of explosive behavior in a person of know age, sex and use of medication, which comprises:

an electroencephalographic machine having a plurality of electrodes adapted for attachment to the scalp of a person in accordance with the American Electroencephalographic Society's Electrode Placement International 10-20 Standard System for measuring a person's brain waves;

means for displaying to said person a plurality of sequentially displayed paradigms and simultaneously measuring the brain waves of said person for each of said displayed paradigms during the time of display;

means for averaging said brain waves to determine the visually evoked potential to said displays of said paradigms;

means for assessing the maximum amplitude, in microvolts, of said visually evoked potential at a point in time approximately 100 msec. after termination of each of said displays of said paradigms;

means for assessing absolute power of the quantitative electroencephalographic activity;

means for conducting a logistic regression analysis of said visually evoked potential approximately at 100 msec. after termination of each of said displays of said paradigms, said electroencephalographic activity, and said person's age, sex, and whether said person is taking any medication, to establish a predictive algorithm; and means for computing the probability of explosive behavior using said algorithm.

4. The apparatus of claim 3 wherein said means for conducting a logistic regression analysis of said visually evoked potential at approximately 100 msec. after termination of each of said displays of said paradigm, said electroencephalographic activity, and said person's age, sex, and whether said person is taking any medication, to establish a predictive algorithm, and means for computing the probability of explosive behavior using said algorithm further comprise:

means for measuring the absolute power of the Delta wave at electrode F4; and means for computing the probability of explosive behavior using the algorithm ln(P[explosive])=−6.2036+0.1194*age+(−0.7567*sex)+0.1743*meds+1.0754*lnDeltaF4+0.2281*maxP100, where (P[explosive]) means the probability of explosive behavior, age means the person's age in years, sex has a value of 0 if said person is a male and a value of 1 if said person is a female, meds has a value of 1 if said person is taking anti-psychotic medications and 0 if not taking said medications, DeltaF4 means the log of the absolute power of the Delta frequency band taken at electrode F4, and maxP100 means the maximum amplitude, in microvolts of said visually evoked potential at a point in time approximate 100 msec. after termination of the displays of said paradigms.

5. A method of determining the probability of explosive behavior in a person of known age, sex and known not to be using medication at the time of testing, using an electroencephalographic machine operable for reading human brain waves, a computer operable for receiving the output of said electroencephalographic machine, a device operable to display a paradigm of a pre-selected design, illumination, and frequency, said computer also capable of synchronizing the recording and averaging said brains waves when the paradigm is illuminated, which comprises:

attaching electrodes of an electroencephalographic machine to the scalp of a person in accordance with the American Electroencephalographic Society's Electrode Placement International 10-20 Standard System for measuring a person's brain waves;

positioning said person to view a paradigm to visually evoke a potential in said person's brain;

displaying to said person a plurality of sequentially displayed paradigms and simultaneously measuring the brain waves of said person for each of said displayed paradigms during the time of display;

averaging said brain waves to determine the visually evoked potential to said displays of said paradigms;

measuring the maximum amplitude, in microvolts, of said visually evoked potential at a point in time approximately 100 msec. after termination of each of said displays of said paradigms;

measuring the absolute power of the Alpha frequency band at electrode F3 and the Delta and Alpha frequency bands at electrode F4; and computing the probability of explosive behavior using the algorithm ln(P[explosive])=−8.0905+0.1348*age+(0.7848*sex)+1.4233*lnDeltaF4+(−2.3854*lnAlphaF3)+2.4054*lnAlphaF4+0.2521*maxP100, where (P[explosive]) means the probability of explosive behavior, age means the person's age in years, sex has a value of 0 if said person is a male and a value of 1 if said person is a female, AlphaF3 means the amplitude of the Alpha brain wave taken at electrode F3, AlphaF4 means the log of absolute power of the Alpha frequency band taken at electrode F4, DeltaF4 means the log of the absolute power of the Delta frequency band taken at electrode F4, and maxP100 means the maximum amplitude, in microvolts of said visually evoked potential at a point in time approximately 100 msec. after termination of the displays of said paradigms.

6. An apparatus for determining the probability of explosive behavior in a person of known age, sex and known not to be using medication, which comprises:

an electroencephalographic machine having a plurality of electrodes adapted for attachment to the scalp of a person in accordance with the American Electroencephalographic Society's Electrode Placement International 10-20 Standard System for measuring a person's brain waves;

means for displaying to said person a plurality of sequentially displayed paradigms and simultaneously measuring the brain waves of said person for each of said displayed paradigms during the time of display;

means for averaging said brain waves to determine the visually evoked potential to said displays of said paradigms;

means for assessing the maximum amplitude, in microvolts, of said visually evoked potential at a point in time approximately 100 msec. after termination of each of said displays of said paradigms;

means for measuring the amplitude of the Delta wave at electrode F4;

means for computing the probability of explosive behavior using the algorithm ln(P[explosive])=−8.0905+0.1348*age+(−0.7848*sex)+1.4233*lnDeltaF4+(−2.3854*lnAlphaF3)+2.4054*lnAlphaF4+0.2521*maxP100, where (P[explosive]) means the probability of explosive behavior, age means the person's age in years, sex has a value of 0 if said person is a male and a value of 1 if said person is a female, AlphaF3 means the log of the absolute power of the Alpha frequency band taken at electrode F3, AlphaF4 means the log of the absolute power of the Alpha frequency band taken at electrode F4, DeltaF4 means the log of the absolute power of the Delta frequency band taken at electrode F4, and maxP100 means the maximum amplitude, in microvolts of said visually evoked potential at a point in time approximately 100 msec. after termination of the displays of said paradigms.

7. A method of determining the probability of explosive behavior in a person of known age, sex and known to be using medication at the time of testing, using an electroencephalographic machine operable for reading human brain waves, a computer operable for receiving the output of said electroencephalographic machine, a device operable to display a paradigm of a pre-selected design, illumination, and frequency, said computer also capable of synchronizing the recording and averaging said brains waves when the paradigm is illuminated, which comprises:

attaching the electrodes of an electroencephalographic machine to the scalp of a person in accordance with the American Electroencephalographic Society's Electrode Placement International 10-20 Standard System for measuring a person's brain waves;

positioning said person to view a paradigm to visually evoke a potential in said person's brain;

displaying to said person a plurality of sequentially displayed paradigms and simultaneously measuring the brain waves of said person for each of said displayed paradigms during the time of display;

averaging said brain waves to determine the visually evoked potential to said displays of said paradigms;

measuring the maximum amplitude, in microvolts, of said visually evoked potential at a point in time approximately 100 msec. after termination of each of said displays of said paradigms;

measuring the absolute power of the Alpha frequency band at electrodes CZ and F4, and the Delta waves at electrodes F4, O2 and T6; and computing the probability of explosive behavior using the algorithm ln(P[explosive])=−3.6891+(−0.0211*age)+6.0591*sex+(−2.214*lnAlphaCZ)+2.3227*lnDeltaF4+2.4516*lnAlphaF4+2.1643*lnDeltaO2+(−3.0554*lnDeltaT6)+(1.6841*sex*lnDeltaO2 P[explosive] means the probability of explosive behavior, age means the person's age in years, sex has a value of 0 if said person is a male and a value of 1 if said person is a female, AlphaCZ means the log of the absolute power of the Alpha frequency band taken at electrode CZ, AlphaF4 means the log of the absolute power of the Alpha frequency band taken at electrode F4, DeltaF4 means the log of the absolute power of the Delta frequency band taken at electrode F4, DeltaO2 means the log of the absolute power of the Delta frequency band taken at electrode O2, and DeltaT6 means the log of the absolute power of the Delta frequency band taken at electrode T6.

8. An apparatus for determining the probability of explosive behavior in a person of know age, sex and known to be using medication, which comprises:

an electroencephalographic machine having a plurality of electrodes adapted for attachment to the scalp of a person in accordance with the American Electroencephalographic Society's Electrode Placement International 10-20 Standard System for measuring a person's brain waves;

means for displaying to said person a plurality of sequentially displayed paradigms and simultaneously measuring the brain waves of said person for each of said displayed paradigms during the time of display;

means for averaging said brain waves to determine the visually evoked potential to said displays of said paradigms;

means for assessing the maximum amplitude, in microvolts, of said visually evoked potential at a point in time representing 100 msec. after termination of each of said displays of said paradigms;

means for measuring the absolute power of the Delta frequency band at electrode F4;

means for computing the probability of explosive behavior using the algorithm $\ln(P[\text{explosive}]) = -8.0905 + 0.1348*\text{age} + (-0.7848*\text{sex}) + 1.4233*\ln\text{DeltaF4} + (-2.3854*\ln\text{AlphaF3}) + 2.4054*\ln\text{AlphaF4} + 0.2521*\text{maxP100}$, where (P[explosive]) means the probability of explosive behavior, age means the person's age in years, sex has a value of 0 if said person is a male and a value of 1 if said person is a female, AlphaF3 means the log of the absolute power of the Alpha frequency band taken at electrode F3, AlphaF4 means the log of the absolute power of the Alpha frequency band taken at electrode F4, DeltaF4 means the log of the absolute power of the Delta frequency band taken at electrode F4, and maxP100 means the maximum log of the absolute power, in microvolts of said visually evoked potential at a point in time approximately 100 msec. after termination of the displays of said paradigms.

* * * * *